United States Patent
Haje

(10) Patent No.: US 7,465,167 B2
(45) Date of Patent: Dec. 16, 2008

(54) METHOD AND DEVICE FOR POSITIONING GUM LINE ABOUT DENTAL REPLACEMENT TEETH SURFACES

(76) Inventor: Emad El Haje, 1800 Eye St., Suite 801, Washington, DC (US) 20006

( * ) Notice: Subject to any disclaimer, the term of this patent is extended or adjusted under 35 U.S.C. 154(b) by 675 days.

(21) Appl. No.: 10/774,451

(22) Filed: Feb. 10, 2004

(65) Prior Publication Data

US 2005/0175962 A1 Aug. 11, 2005

(51) Int. Cl.
*A61C 5/14* (2006.01)
(52) U.S. Cl. ...................................... 433/136
(58) Field of Classification Search ................ 433/136, 433/138, 139, 18, 11
See application file for complete search history.

(56) References Cited

U.S. PATENT DOCUMENTS

| | | | | |
|---|---|---|---|---|
| 3,238,620 A | * | 3/1966 | Robertson | 433/40 |
| 4,764,377 A | * | 8/1988 | Goodson | 424/435 |
| 5,829,974 A | * | 11/1998 | Brosius | 433/15 |
| 5,976,439 A | * | 11/1999 | Mahoney et al. | 264/181 |

* cited by examiner

*Primary Examiner*—Cris L Rodriguez
*Assistant Examiner*—Sunil K Singh
(74) *Attorney, Agent, or Firm*—Barnes & Thornburg LLP

(57) ABSTRACT

A gum packing tool made from a sterilizable elastic endless strand which can be enlarged by tensioning the strand so that the strand can fit over a patient's tooth and when the tension is released, the strand will be tensioned against the sides of the tooth, whereupon the tool can be moved along the side of the tooth to come in contact with the soft tissue gum line so as to provide a tamping surface for forcing the soft tissue gum against the root portions of the tooth. The method for utilizing the tool is also provided.

2 Claims, 1 Drawing Sheet

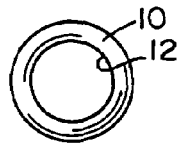 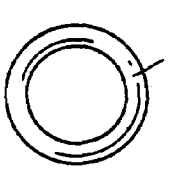 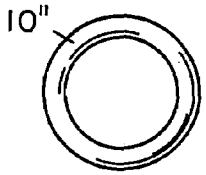 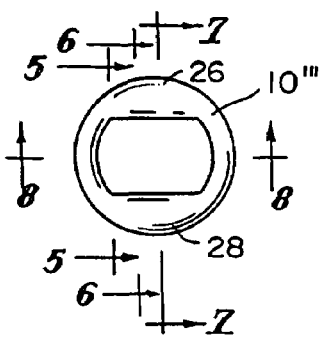
FIG.1  FIG.2  FIG.3  FIG.4
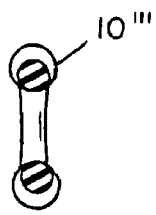  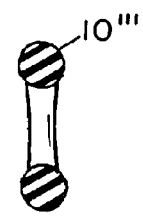 
FIG.5  FIG.6  FIG.7  FIG.8
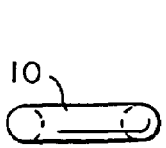 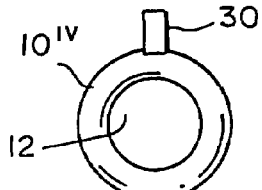 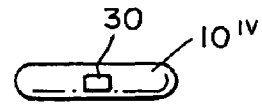
FIG.9  FIG.10  FIG.11
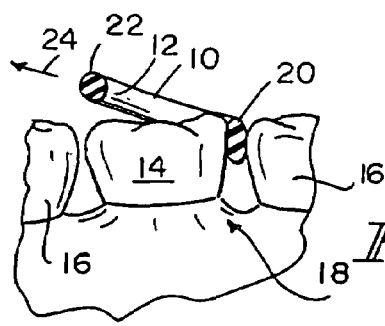 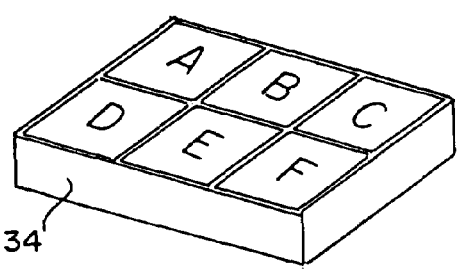
FIG.13  FIG.12
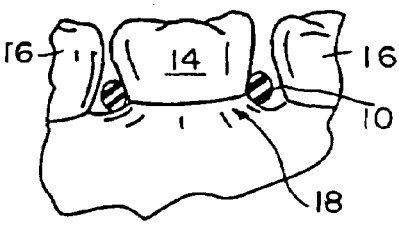
FIG.14  FIG.15

METHOD AND DEVICE FOR POSITIONING GUM LINE ABOUT DENTAL REPLACEMENT TEETH SURFACES

This invention relates to a device and method for packing dental soft gum tissue around prosthetic teeth such as dental caps and implants.

BACKGROUND AND SUMMARY OF THE INVENTION

When prosthetic tooth caps or implants are placed in the mouth, the soft tissue gum line around the prosthetic must be tamped around the prosthetic. Currently this tamping is accomplished utilizing a round string-like retraction cord that the dentist strings around the prosthetic on top of the soft gum tissue. A tamping instrument is then used to push down on the cord to force the soft gum tissue against the root exposed portion of the prosthetic tooth. Keeping the retraction cord in place is difficult, since the dentist must hold two ends of the cord as it is tightened around the tooth. The patient through tongue action and lip movement, tends to cause the cord to be lifted upwardly. Likewise, tightening of the cord around the prosthetic tooth is difficult, due to the lack of space between the tooth and tongue and lip and due to the lack of space inside the mouth.

This invention relates to a replacement for the retraction cord. A resilient and stretchable endless strand tool of dense material is utilized instead of the cord. The endless strand needs to be sterilizable and comes in various lengths and thicknesses. Because it is made of a dense material, reduction or elimination of pockets in the strand where germs can lodge is avoided. The dentist stretches the endless strand of material around a single tooth prosthetic and pushes it over and along the sides of the prosthetic tooth until the endless strand meets the soft gum tissue. Because of its elastic and stretchable nature the endless strand stretches around the tooth prosthetic and is held taut around all side surfaces of the prosthetic. Because of its round cross-section, the endless strand can be rolled along the prosthetic tooth side surfaces down to the soft tissue gum line.

Because of its elastic nature, the endless strand tool can be tensioned by a dental practitioner pulling on opposite sides of the endless strand to elongate the endless strand to permit it to be placed over and around the tooth prosthetic and when the tensioning is released, the endless strand returns to its original length whereby it grasps the tooth prosthetic tightly along its sides.

If the cross-sectional area of the endless strand is circular, this will allow a dental practitioner to move the endless strand tool along the tooth sides toward the root portion of the tooth prosthetic by rolling until the endless strand tool comes into contact with the soft gum tissue. Once in place against the soft gum tissue, the endless strand tool can be tamped by a dental tool to force the soft gum tissue below it against the root portion of the dental prosthetic.

Additional possible modifications of the endless strand tool include having at least one extending tab which can be gripped by the dental practitioner to stretch the endless strand to provide for easy insertion around the tooth and easy removal of the endless strand from around the tooth after the tamping operation is finished. If two opposed tabs are provided on the endless strand, they can be griped and pulled apart to provide for an easy way to tension and elongate the endless strand whereby it can be more easily slipped over the top of the tooth prosthetic for ease of insertion over the tooth prosthetic as well as for ease in removal.

As the soft gum tissue varies in spacing from the tooth prosthetic, having various width strands can accommodate for the difference in gapping of the gum tissue from the tooth surface. As a tooth prosthetic is desirable closely fitted to the adjacent teeth, the space between teeth may be quite narrow. In such cases, portions of the endless strand can be provided to have a narrow thickness to pass through the narrow space between prosthetic and adjacent tooth while having a wider thickness along the sides of the prosthetic. The tensioning step for insertion can accent the narrowing of the narrow thickness as the endless strand is inserted over the tooth surface while releasing of the tension allows the endless strand to resume its original configuration to fill the enlarged space gap between root portions between teeth.

Other objects, advantages and novel features of the present invention will become apparent from the following detailed description of the invention when considered in conjunction with the accompanying drawings.

BRIEF DESCRIPTION OF THE DRAWINGS

FIG. 1 shows a plan view of a small sized endless strand tamping tool according to the invention;

FIG. 2 shows a plan view of a medium sized endless strand tamping tool according to the invention;

FIG. 3 shows a plan view of large sized endless strand tamping tool according to the invention;

FIG. 4 shows a plan view of an endless strand tool with thickened opposed cross-sectional areas;

FIGS. 5, 6, 7, and 8 shows cross-sectional views of the FIG. 4 embodiment taken along section lines 5, 6, 7 and 8, respectively;

FIG. 9 shows a side view of the embodiment of FIG. 1;

FIG. 10 shows a plan view of an endless strand tool provided with tabs along its sides.

FIG. 11 is a side view of the embodiment of FIG. 10.

FIG. 12 is a view of a kit containing six compartments for storage of various sized and shaped endless strand tools;

FIG. 13 shows a side view of a patient's mouth with the first step of inserting the endless strand tool;

FIG. 14 shows a side view of a patient's mouth with the second step of inserting the endless strand tool; and FIG. 15 shows a side view of a patient's mouth with the final step of inserting the endless strand tool.

DETAILED DESCRIPTION OF THE DRAWINGS

When dentist install prosthetic tooth caps or dental implants into a patient's jaw, the soft gum tissue around the root portion of the prosthetic is spread open to allow for insertion of the prosthetic. After insertion and seating of the prosthetic tooth, the soft gum tissue needs to be tamped around the root portion of the prosthetic so that the soft gum tissue will prevent entry of germs and food particles between the root portion of the prosthetic and the soft gum issue. Likewise, dentists separate the soft gum tissue away from the root portions of teeth during some dental procedures such as deep scaling and periodontal work.

Current procedure calls for tamping the soft gum tissue around the root portion of the tooth after insertion of the prosthetic tooth or after the dental procedures. To aid in tamping of the soft gum tissue around the root portion of a patient's tooth, a dentist takes a long round string material and wraps it tight about the root portion of the tooth and holds the string around the sides of the tooth at the soft gum tissue line and then takes a tamper tool and presses down on the string causing the string to press the soft gum tissue about the root portions of the tooth. The use of a string as a tamping tool has its problems because the dentist has to hold both ends of the string at the same time as he tamps down on the string. One way to hold the string is to wrap one end of the string around the thumb of one hand, then wrap the string around the root portion of the tooth, wrap the other end of the string around the dentist fore finger. Moving the thumb away from the fore finger tightens the string around the root portion of the tooth. The tightening of the string around the dentist's fingers is painful. Furthermore, when a patient moves its tongue or lips, contact of the tongue or lips with the string or dentist fingers tends to move the string from adjacent the gum line. Likewise, having to keep the dentist's hand in the patient's mouth causes discomfort and is difficult since there is not much room to both hold the string with one hand and the tamper tool in the other.

The invention herein provides for replacement of the string with an endless flexible strand tool which can be stretched to be enlarged to pass over the head of a prosthetic tooth and slid along the sides of the tooth down to the gum line where the strand is relaxed and assumes a tight fit against the bottom portion of the prosthetic tooth and strays there without holding, leaving both of the dentist hands free for the tamping action.

FIG. 1 shows an endless flexible strand tool 10 which can be used to replace the string. The strand tool 10 has a round cross-section as shown in FIG. 10 to assist in its movement toward the root of the tooth prosthetic as will be explained infra. The material of the endless flexible strand should be flexible to allow it to be stretched so as to increase its length and thus its inside opening 12 to allow for insertion over the top of a tooth prosthetic. The material must be returnable to its original size upon release of the stretching forces so the endless strand will grasp the sides surfaces of the tooth prosthetic. The material should be sterilizable to avoid germs in the patient's mouth. Ideally the endless strand tool can be sterilized at the factory and placed in a sealed envelope. Alternatively, the material could be sterilized in the normal autoclave dental sterilizer in the dentist's office. The material should thus be quite dense to avoid pockets therein, which pockets could provide a home for dirt, germs and other contaminants.

Reference to FIGS. 13-15 will provide an understanding of how the dense flexible endless strand tool 10 is placed over a prosthetic tooth 20 in a patient's mouth. The first step (FIG. 13) is to place one end 20 of the dense flexible endless strand tool between the prosthetic tooth 20 and its adjoining tooth 16. An opposite side 22 of the flexible endless strand tool 10 is then pulled in the direction of the arrow 24 to cause the inner opening 12 to be enlarged so that the dense flexible endless strand tool can pass over the top of the prosthetic tooth 14 to assume the position shown in FIG. 14. Once the dense flexible endless strand tool 10 passes over the top of the prosthetic tooth 14, the stretching can be relaxed to allow the dense endless flexible strand tool to grip the sides of the prosthetic tooth 14 as shown in FIG. 14. While the start portion is shown to be between teeth, the start could be at the side of the tooth and the stretching would automatically thin that portion of the tool between teeth as the tool is slipped over the tooth. Preferably the cross-section of the dense flexible endless strand 10 is round (as shown in FIG. 9) which will enable the dentist to roll the dense flexible endless strand tool downward to the gum line 18 (see FIG. 15). The dentist can then take a tamper tool (not shown) and push downward on the dense flexible endless strand tool to force the soft gum tissue at the gum line 18 against the side surfaces of the prosthetic tooth 14. While FIGS. 13-15 show a lower dental jaw configuration for use of the dense flexible endless strand tool, it is contemplated that the dense flexible endless strand can be used on an upper jaw. In such an installation of the dense flexible endless strand tool will be rolled upward to the gum line.

FIGS. 2 and 3 show the dense flexible endless strand tool 10' and 10" with different lengths to accommodate different sized teeth. Cuspids, incisors, molars have different surface areas. Likewise, children's teeth can be smaller than adult teeth etc. While these views show the cross-sectional areas to be alike, they could, of course, be of different thickness.

FIG. 4 shows a dense flexible endless strand tool where the cross-sectional area is not uniform and where there are enlarged opposing cross-sectional areas 26 and 28. This type of tool can be used where the space between the soft gum and gum tissue varies. Ideally the cross-sectional area of the tool remains circular (note FIGS. 5-8) for ease in the rolling of the dense flexible strand tool along the sides of a tooth. Of course, the cross-sectional area does not have to be continually variable. This would allow the center of the widened portion to be cylindrical in cross-section, with conical ends.

FIGS. 10 and 11 show a dense flexible strand tool $10^{iv}$ with tabs 30 and 32 extending therefrom. They can be of different lengths or loop shaped to provide better gripping therefore. These tabs are provided to give the dentist a place to grip the dense flexible strand tool when he attempts to tension the tool to enlarge the opening 12. The tabs 30 and 32 should be thin so as to be wrapable about the tool $10^{iv}$ when the tool $10^{iv}$ is being rolled along the side surface of a tooth to move it down to the gum line as explained, supra. Also these tabs 30 and 32 can be used to pull the tool 10 off the tooth after the dentist has tamped down the soft gum tissue. While two opposing tabs 30 and 32 are shown, tools with only one tab are contemplated.

FIG. 12 shows a kit with compartments A-F for holding various sized dense flexible strand tools (e.g., 10, 10', 10"); tools with variable thickness (10"); tools $10^{iv}$ with tabs and tools having different thickness. During a dental procedure, these compartments will be filled with sterilized differently configured dense flexible strand tools and the dentist can select from the assortment, the desired tool configuration based on the size of the tooth and gum line spacing occurring.

While the dense flexible strand tool has been shown with a preferred circular cross-sectional configuration, such a cross-section could be oval, square or rectangular. When square or rectangular in cross-section, having the corners thereof rounded will assist in rolling of the dense flexible strand tool along the sides of the tooth, as explained supra.

During periodontal work and other dental surgery procedures, patient pain and/or hygiene are of importance. In such situations it would be desirable to have the dense flexible strand tool coated with either an antiseptic, vaso-constrictor and/or an analgesic. These coatings would release medicines and/or pain killers to the area of the gum line.

It is also within the scope of the invention to have the dense flexible strand be made of a biodegradable material which could be left at the gum line and slowly absorbed by the human body.

Thus during periodontal surgery pain suppression and antibiotics would be administered and the dense flexible strand left at the tooth root site in the jaw while the gums healed, the strand would be absorbed.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A method of packing soft tissue gums around a tooth comprising the steps of:
    selecting a gum packing assisting tool comprising
        an endless strand of material,
        the endless strand being made of a material which is easily sterilized,
        the endless strand being made of a flexible dense material which stretches when under tension and which returns to its original shape when the tension is released, and which admits of few, if any, pockets for housing germs and contaminants therein,
        wherein the length of the endless strand is less than the circumference of tooth around which soft gum is to be forced around, so that the endless strand can be tensioned to allow the endless strand to be placed over and encircle the tooth and to tightly grip the edges of the tooth when the tension is released,
        wherein the endless strand tool has portions of its cross-section to be of circular configuration so as to facilitate rolling downward of the endless strand over the sides of a tooth to the gum line of the patient,
    tensioning the gum packing assisting tool to stretch the tool,
    placing the stretched tool over and around a tooth,
    releasing the tension on the tool,
    moving the tool along the tooth until the tool touches the soft tissue gum adjacent the root portion of the tooth,
    tamping the tool to move the touching soft tissue gum against the root portion of the tooth, and
    removing the tool from the tooth.

2. The method of claim 1 wherein the moving of the tool is accomplished via rolling of the endless strand of material toward a gum line.

* * * * *